United States Patent
Kim et al.

(10) Patent No.: US 11,547,381 B2
(45) Date of Patent: Jan. 10, 2023

(54) WEARABLE RESPIRATORY MONITORING SYSTEM BASED ON RESONANT MICROPHONE ARRAY

(71) Applicant: UNIVERSITY OF SOUTHERN CALIFORNIA, Los Angeles, CA (US)

(72) Inventors: Eun Sok Kim, Rancho Palos Verdes, CA (US); Anton Andreevich Shkel, Irvine, CA (US)

(73) Assignee: University of Southern California, Los Angeles, CA (US)

( * ) Notice: Subject to any disclaimer, the term of this patent is extended or adjusted under 35 U.S.C. 154(b) by 422 days.

(21) Appl. No.: 16/156,689

(22) Filed: Oct. 10, 2018

(65) Prior Publication Data

US 2019/0105011 A1    Apr. 11, 2019

Related U.S. Application Data

(60) Provisional application No. 62/570,546, filed on Oct. 10, 2017.

(51) Int. Cl.
*A61B 7/00* (2006.01)
*H04R 1/40* (2006.01)
(Continued)

(52) U.S. Cl.
CPC .............. *A61B 7/003* (2013.01); *A61B 5/002* (2013.01); *A61B 5/08* (2013.01); *A61B 5/746* (2013.01); *G06K 9/00536* (2013.01); *G06K 9/6297* (2013.01); *G06V 30/194* (2022.01); *G10L 25/66* (2013.01); *H04R 1/028* (2013.01); *H04R 1/406* (2013.01); *H04R 1/46* (2013.01); *H04R 3/005* (2013.01); *H04R 3/04* (2013.01); *A61B 5/0823* (2013.01); *A61B 5/6823* (2013.01);
(Continued)

(58) Field of Classification Search
None
See application file for complete search history.

(56) References Cited

U.S. PATENT DOCUMENTS 6,498,854 B1 *   12/2002   Smith ...................... A61B 7/04
                                                    381/67
2002/0183642 A1 * 12/2002   Murphy ................... A61B 8/00
                                                    600/532
(Continued)

OTHER PUBLICATIONS

Shkel, A.A. et al., "A Resonant Piezoelectric Microphone Array for Detection of Acoustic Signatures in Noisy Environments," MEMS 2015, Estoril, Portugal, pp. 917-920.
(Continued)

*Primary Examiner* — Jacqueline Cheng
*Assistant Examiner* — Jairo H Portillo
(74) *Attorney, Agent, or Firm* — Brooks Kushman P.C.

(57) ABSTRACT

A method for continuous acoustic signature recognition and classification includes a step of obtaining an audio input signal from a resonant microphone array positioned proximate to a target, the audio input signal having a plurality of channels. The target produces characterizing audio signals depending on a state or condition of the target. A plurality of features is extracted from the audio input signal with a signal processor. The plurality of features is classified to determine the state of the target. An acoustic monitoring system implementing the method is also provided.

25 Claims, 12 Drawing Sheets

(51) Int. Cl.

| | |
|---|---|
| *H04R 3/00* | (2006.01) |
| *H04R 1/46* | (2006.01) |
| *H04R 3/04* | (2006.01) |
| *A61B 5/08* | (2006.01) |
| *A61B 5/00* | (2006.01) |
| *G06K 9/00* | (2022.01) |
| *G06K 9/62* | (2022.01) |
| *G10L 25/66* | (2013.01) |
| *H04R 1/02* | (2006.01) |
| *G06V 30/194* | (2022.01) |
| *A61B 7/04* | (2006.01) |
| *A61B 7/02* | (2006.01) |
| *H04R 17/02* | (2006.01) |
| *H04R 19/04* | (2006.01) |
| *G10L 25/24* | (2013.01) |
| *G06N 3/08* | (2006.01) |
| *G06N 7/00* | (2006.01) |
| *G06N 20/10* | (2019.01) |

(52) U.S. Cl.
CPC ........... *A61B 5/6831* (2013.01); *A61B 5/6832* (2013.01); *A61B 5/725* (2013.01); *A61B 5/7253* (2013.01); *A61B 5/7264* (2013.01); *A61B 7/026* (2013.01); *A61B 7/04* (2013.01); *A61B 2562/0204* (2013.01); *G06N 3/08* (2013.01); *G06N 7/005* (2013.01); *G06N 20/10* (2019.01); *G10L 25/24* (2013.01); *H04R 17/02* (2013.01); *H04R 19/04* (2013.01)

(56) References Cited

U.S. PATENT DOCUMENTS

| | | | | |
|---|---|---|---|---|
| 2005/0246169 | A1* | 11/2005 | Lahti | G10L 25/87 704/215 |
| 2006/0198533 | A1* | 9/2006 | Wang | A61B 7/00 381/94.1 |
| 2007/0195905 | A1* | 8/2007 | Schatz | H04L 1/004 375/265 |
| 2013/0090567 | A1* | 4/2013 | Lee | A61B 7/04 600/529 |
| 2013/0131465 | A1* | 5/2013 | Yamamoto | A61B 5/7271 600/300 |
| 2014/0126732 | A1* | 5/2014 | West | H04R 1/46 381/67 |
| 2014/0171815 | A1* | 6/2014 | Yang | A61B 5/4818 600/529 |
| 2014/0257051 | A1* | 9/2014 | Cam | A61B 5/7267 600/301 |
| 2014/0276229 | A1* | 9/2014 | Ikeda | A61B 7/003 600/586 |

OTHER PUBLICATIONS

Shkel, A.A. et al., "Wearable Low-Power Wireless Lung Sound Detection Enhanced by Resonant Transducer Array for Pre-Filtered Signal Acquisition," Transducers 2017, Kaohsiung, Taiwan, pp. 842-845.

Baumgartel, L. et al., "Resonance-Enhanced Piezoelectric Microphone Array for Broadband or Prefiltered Acoustic Sensing," J. of Microelectromechanical Systems, v. 22, n. 1, 2013, pp. 107-114.

* cited by examiner

WEARABLE RESPIRATORY MONITORING SYSTEM BASED ON RESONANT MICROPHONE ARRAY

CROSS-REFERENCE TO RELATED APPLICATION

This application claims the benefit of U.S. provisional application Ser. No. 62/570,546 filed Oct. 10, 2017, the disclosure of which is incorporated in its entirety by reference herein.

TECHNICAL FIELD

In at least one aspect, the present invention is related to methods and systems for continuous acoustic signature recognition and classification, and in particular, to methods and systems for monitoring respiration in a subject.

BACKGROUND

With the emergence of Internet of Things (IoT), personal digital assistants, wearable devices, and wireless sensor networks, we are seeing a boom in the ubiquitous presence of sensors and environmental data. With these trends, there is a constant tradeoff between functionality and power consumption, which has driven development of battery and energy harvesting technologies, as well as power-efficient processing electronics. The method proposed in this document addresses these limitations of existing technologies by performing a portion of the processing passively in the transducer itself, rather than in the power-hungry digital electronics.

Early detection of asthma attacks can be most effectively achieved by continuous monitoring of lung sounds with a stethoscope. However, there is currently no wearable, wirelessly-connected, always-on lung-sound tracker as effective as evaluation by a trained clinician. An ultra-low-power device with continuous monitoring of the acoustic signature of sensed lung sounds can identify precursors of lung-related health problems such as asthma attacks, and automatically notify for assistance.

Accordingly, there is a need for improved methods and systems for monitoring respiration sounds in a subject.

SUMMARY

In at least one aspect, the present invention provides an array-based respiratory monitoring system, which realizes continuous acoustic signature recognition and classification using a low-power and noise-robust method.

In another aspect, a method for continuous acoustic signature recognition and classification is provided. The method includes a step of obtaining an audio input signal from a resonant microphone array positioned proximate to a target where the audio signal has a plurality of channels. Characteristically, the target produces characterizing audio signals depending on a state or condition of the target. A plurality of features is extracted from the audio input signal. The plurality of features is classified to determine the state of the target.

In another aspect, the method for continuous acoustic signature recognition and classification monitors respiration in a human subject.

In still another aspect, an acoustic monitoring system is provided. The acoustic monitoring system includes a resonant microphone array configured to obtain an audio input signal having a plurality of channels. The resonant microphone array is also configured to pre-filter the audio input signal to form a pre-filtered audio input signal(s). The system also includes a signal processor configured to divide the pre-filtered audio input signal into one or more frames, windowing each of the one or more frames of the pre-filtered audio input signal, transform the pre-filtered audio input signal into a feature vector that is outputted, determine whether the audio input signal matches with a specific sound or sounds through a classification algorithm, and wirelessly send the audio input signal or a notification of detection out to a nearby mobile phone or wireless transceiver.

In still another aspect, a wearable stethoscope for constant monitoring of lung sounds for various applications is provided. The wearable stethoscope includes a resonant microphone array which obviates the need for an acoustic coupler. The wearable stethoscope can be less bulky than a conventional stethoscope with much less power consumption.

DETAILED DESCRIPTION

Figure 1:
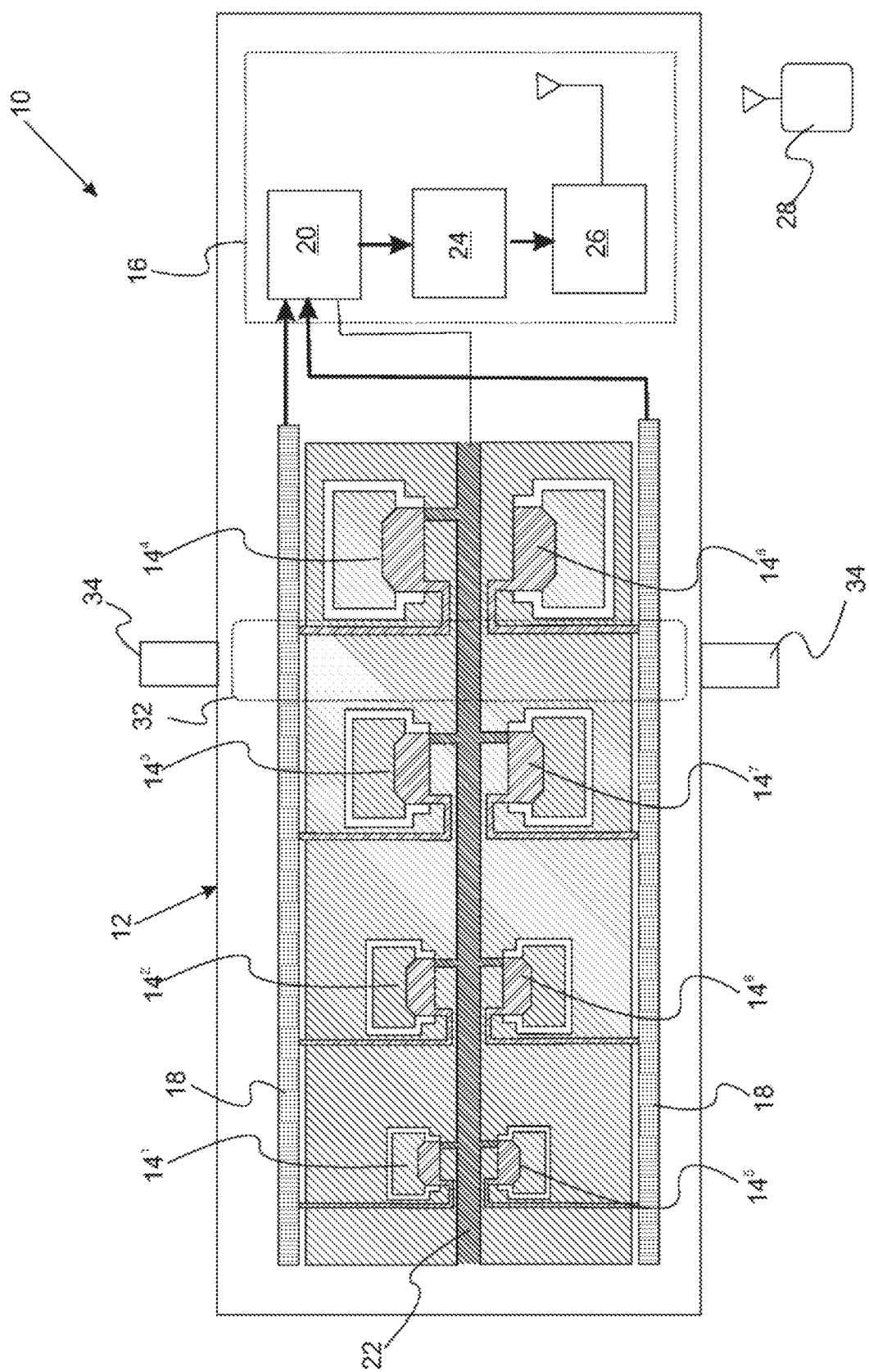
FIG. 1: Schematic cross section of a respiratory monitory system.

Reference will now be made in detail to presently preferred compositions, embodiments and methods of the present invention, which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. Also, unless expressly stated to the contrary: percent, "parts of," and ratio values are by weight; all lower case letters (e.g., i, j, o, p, etc.) are integers 0, 1, 2, 3, 4, 5, or 6; the first use of a symbol carries through to subsequent uses unless defined to the contrary; the description of a group or class of materials as suitable or preferred for a given purpose in connection with the invention implies that mixtures of any two or more of the members of the group or class are equally suitable or preferred; the first definition of an acronym or other abbreviation applies to all subsequent uses herein of the same abbreviation; and, unless expressly stated to the contrary, measurement of a property is determined by the same technique as previously or later referenced for the same property.

It must also be noted that, as used in the specification and the appended claims, the singular form "a," "an," and "the" comprise plural referents unless the context clearly indicates otherwise. For example, reference to a component in the singular is intended to comprise a plurality of components.

Throughout this application, where publications are referenced, the disclosures of these publications in their entireties are hereby incorporated by reference into this application to more fully describe the state of the art to which this invention pertains.

The term "comprising" is synonymous with "including," "having," "containing," or "characterized by." These terms are inclusive and open-ended and do not exclude additional, unrecited elements or method steps.

The phrase "consisting of" excludes any element, step, or ingredient not specified in the claim. When this phrase appears in a clause of the body of a claim, rather than immediately following the preamble, it limits only the element set forth in that clause; other elements are not excluded from the claim as a whole.

The phrase "consisting essentially of" limits the scope of a claim to the specified materials or steps, plus those that do not materially affect the basic and novel characteristic(s) of the claimed subject matter.

With respect to the terms "comprising," "consisting of," and "consisting essentially of," where one of these three terms is used herein, the presently disclosed and claimed subject matter can include the use of either of the other two terms.

It should also be appreciated that integer ranges explicitly include all intervening integers. For example, the integer range 1-10 explicitly includes 1, 2, 3, 4, 5, 6, 7, 8, 9, and 10. Similarly, the range 1 to 100 includes 1, 2, 3, 4 . . . 97, 98, 99, 100.

Abbreviations

"ADC" means analog to digital converter.

"ANN" means Artificial Neural Networks.

"BLE" means Bluetooth Low Energy.

"DCT" means discrete cosine transform.

"IDCT" means inverse discrete cosine transform.

"HMM" means Hidden-Markov Models.

"IoT" means Internet of Things.

"SOI" means silicon-on-insulator.

"SVM" means Support Vector Machines.

In an embodiment, a method for continuous acoustic signature recognition and classification is provided. With reference to FIG. 1, acoustic monitoring system 10 is used to perform the method for monitoring respiration. The method includes a step of obtaining audio input signals from a resonant microphone array 12. Characteristically, resonant microphone array 12 is placed proximate to a target that produces characterizing audio signals depending on a state or condition of the target. Advantageously, the component housing the resonant microphone array 12 is attached to the target (e.g., with an adhesive or strap). In one particularly useful application, the method is used to monitor respiration in a mammalian subject, and in particular, a human subject. In this variation, resonant microphone array 12 is placed on the subject at a location from which audio signals from the lungs can be observed (e.g., the subject's chest or back or trachea). In this variation, conditions such as asthma and wheezing can be monitored. Similarly, the method and system can be used to for automatic speech recognition and the automatic detection of medical acoustic signatures. For example, the method and system can be used to monitor heart sounds to detect murmurs. In still other variations, method and system can be used for automatic monitoring of industrial processes via analysis of acoustic spectral signatures (e.g., leak detection in oil pipelines or monitoring of engine operation). The acoustic monitoring system can advantageously be attached to the target to allow continuous monitoring via a wireless communication link.

Resonant microphone array 12 includes a plurality of resonant microphone $14^j$ where j is 1 to m and m is the total number of resonant microphones. Although the present invention is not limited to any particular number of resonant microphones, typically m is an integer from 3 to 25. In a refinement, m is an integer from 4 to 25. Each resonant microphone $14^j$ provides an audio signal over a corresponding channel. In a variation, the resonant frequencies of the plurality of piezoelectric cantilevers (or any other structures, such as diaphragm, used for a resonant microphone) are spaced between a first predetermined audio frequency and a second audio predetermined frequency where the second predetermined audio frequency is greater than the first predetermined audio frequency. The first predetermined audio frequency and the second predetermined audio frequency are each in the range 20 Hz and 12,000 Hz. In a refinement, the resonant frequencies are evenly between 20 Hz and 12,000 Hz. In further refinement, the resonant frequencies are logarithmically spaced (e.g., with mel scale) between 20 Hz and 12,000 Hz. Characteristically, the resonant microphone array 14 provides prefiltering of the audio input signals, due to highly enhanced sensitivities near the resonant frequencies, to produce pre-filtered audio input signals. In this regard, the resonant microphone array 14 has a plurality of piezoelectric cantilevers or capacitive diaphragms or any other structures that form a plurality of resonant microphones that obtain audio signals and pre-filter the audio signals into a plurality of frequency bands.

This prefiltering is done in acoustic domain with high quality due to the high quality factors of the mechanical resonances of the resonant microphones' cantilever or diaphragm, and gets rid of the need for power-hungry digital electronic filters. A larger number of the resonant microphones is like having a larger number of electronic filters, and offers better classification of the sound, but without increasing power consumption that an electronic filter bank would require for a larger number of filters. The plurality of resonant microphones can include piezoelectric cantilevers (or diaphragms) or a capacitive combination of diaphragm and back plate as set forth below in more detail.

Each pre-filtered audio input signal is provided to a signal processor 16 over a multichannel bus 18 that carries each audio input signal individually over a corresponding conductive path to pre-amplifier and ADC 20. Each of the pre-filtered signal from the resonant microphone is pre-amplified, before being digitized by ADC. ADC 20 converts each audio signal to a digitized pre-filtered audio input signal. FIG. 1 also depicts common bus 22 that is also in electrical communication with ADC 20. Microprocessor 24 acts on the digital pre-filtered audio input signals, and extracts audio features which then are classified into predetermined respiratory states or conditions.

Acoustic features of sound signal are extracted from (a) the waveform in time domain, (b) spectral powers in frequency spectra, or (c) energy contour in time. A key definition of an acoustic feature is that it is characterized by a unique distribution of acoustic energy in the (a) time domain waveform (temporal features), in the (b) spectral domain (spectral features), or in the variation in the spectral domain over time (spectro-temporal features). Features or feature vectors are extracted from sound signal to classify the sound into a certain category. Audio features can be extracted by a variety of signal processing techniques known to those skilled in the art. In a variation, each of the pre-filtered audio input signals (e.g., the digitized pre-filtered audio input signals) are partitioned into one or more frames. A windowing function is then applied to each of the one or more frames of the pre-filtered audio input signal (e.g., the digitized pre-filtered audio input signals). In a refinement, pre-emphasis is performed on the pre-filtered audio input signal that has been windowed and framed typically using a pre-emphasis network to form pre-emphasized audio signals which are typically digitized. For example, a filter (e.g., a filter algorithm) can be applied for pre-emphasis of high-frequency components. In a variation, the step of pre-emphasis on the pre-filtered audio signal includes boosting one or more frequencies of the pre-filtered audio signal relative to other frequencies of the pre-filtered audio signal to minimize transmission distortion.

Microprocessor 24 transforms the pre-filtered audio input signal (e.g., the digitized pre-filtered audio input signals) into a feature vector or plurality of features. In still a further refinement, microprocessor 24 outputs the feature vector. In still a further refinement, microprocessor 24 determines whether the audio input signal matches with a specific sound or sounds through a classification algorithm that may employ machine-learning. The classification can provide a determination as to the state or condition of the target; for example, a determination as to whether or not the subject is wheezing or is about to have an asthma attack. In an industrial scenario, the method can determine if a fluid conduit is leaking or is fluid flowing in the conduit as designed. Examples of classification algorithms includes, but are not limited to, Naive Bayes classifiers, Hidden-Markov Models, Artificial Neural Networks, and Support Vector Machines, and the like. In yet another refinement, the audio input signal or a notification of detection out are wirelessly sent via wireless interface 26 to a nearby mobile phone or wireless transceiver 28.

In this regard, microprocessor 24 may apply an inverse discrete cosine transform (DCT) to the pre-emphasized audio signals to evaluate the real-spectrum of the pre-emphasized audio signal (e.g., the digitized pre-filtered audio input signals). Digital filter banks are then applied to estimate the filter energies at each filter bank frequency. The logarithm of the filter energies is passed through an inverse-DCT to transform them into the cepstral domain. A feature vector is then calculated which includes a vector of cepstral coefficients. The first several cepstral features (e.g., the first 3 to 10 cepstral coefficients) are taken as the resulting feature vector.

In a variation, the step transforming the pre-filtered audio input signal into the feature vector includes directly calculating a spectral energy of the pre-filtered audio input signal in the time-domain to reduce a number of computations to an order of n instructions, rather than an order of square of n instructions, which results in an increase in processing speed and battery life.

FIG. 1 also depicts adhesive layer 32 and strap 34, either of which can secure the acoustic monitoring system to the target, for example, a human subject's chest.

Figure 2A:
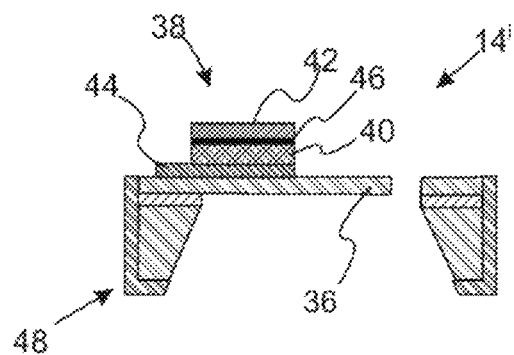
FIG. 2A: Schematic cross section of a resonant microphone having a cantilever component.
Figure 2B:
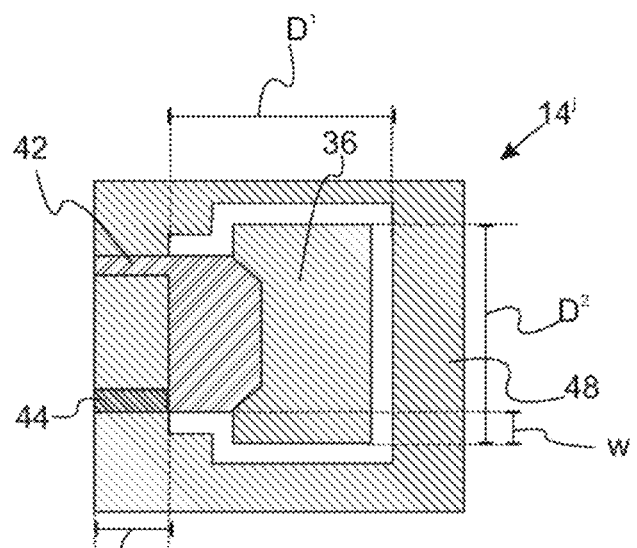
FIG. 2B: Schematic top view of a resonant microphone having a cantilever component.

With reference to FIGS. 2A and 2B, schematic illustrations of a resonant microphone are provided. Resonant microphone 14' includes cantilever paddle 36. Piezoelectric assembly 38 is resonant microphone 14'. Piezoelectric assembly 38 includes a piezoelectric layer 40 interposed between top electrical contact 42 and bottom electrical contact 44. Dielectric layer 46 is interposed between top electrical contact 42 and piezoelectric layer 40. Cantilever paddle 36 has an end supported by base 48. The $D^1$, $D^2$, and w provide dimensions of cantilever paddle 36. These dimensions are used to set the resonant frequency of the resonant microphone. Typically, $D^1$, $D^2$, are each independently from about 0.5 to about 10 mm and w is from about 0.1 to about 3 mm. Moreover, l is a dimension of base 48 supporting cantilever paddle 36. Typically, l is from about 0.2 to 1 mm. The open gap around cantilever paddle 36 needs to be as narrow as possible to prevent leakage of acoustic pressure through gap which affects microphone sensitivities at low frequencies.

The following examples illustrate the various embodiments of the present invention. Those skilled in the art will recognize many variations that are within the spirit of the present invention and scope of the claims.

Figure 3A:
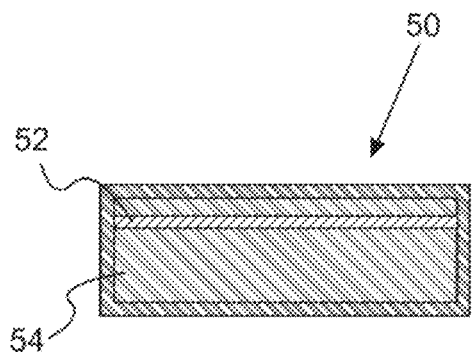
FIGS. 3A, 3B, 3C, 3D, and 3E: Diagram showing fabrication processes of resonant MEMS microphone.
Figure 3C:
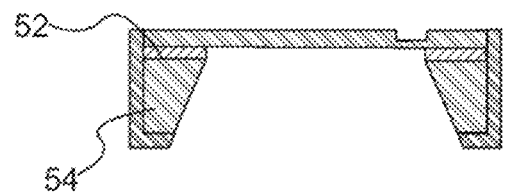
Figure 3B:
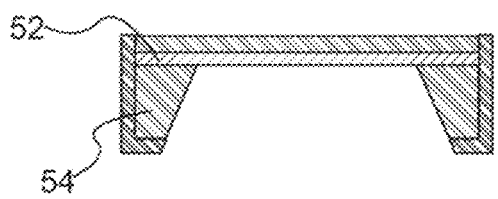

The resonant microphone array set forth above is fabricated on a silicon-on-insulator (SOI) wafer 50 with 4.5 μm thick device layer (FIG. 3A). The SOI's oxide layer 12 buried in silicon 54 serves as an etch-stop for anisotropic potassium hydroxide KOH backside etching as depicted in FIG. 3B. An SOI wafer is chosen as the substrate because of the accuracy and consistency of the SOI device layer thickness. This allows for reliable control of cantilever dimension and frequency characteristics.

Figure 3D:
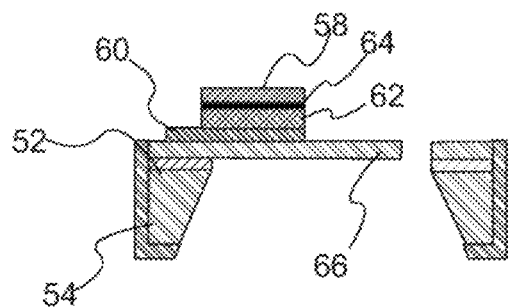
Figure 3E:
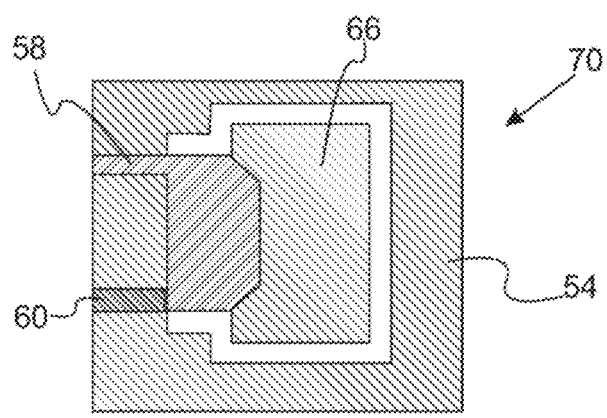
Figure 4A:
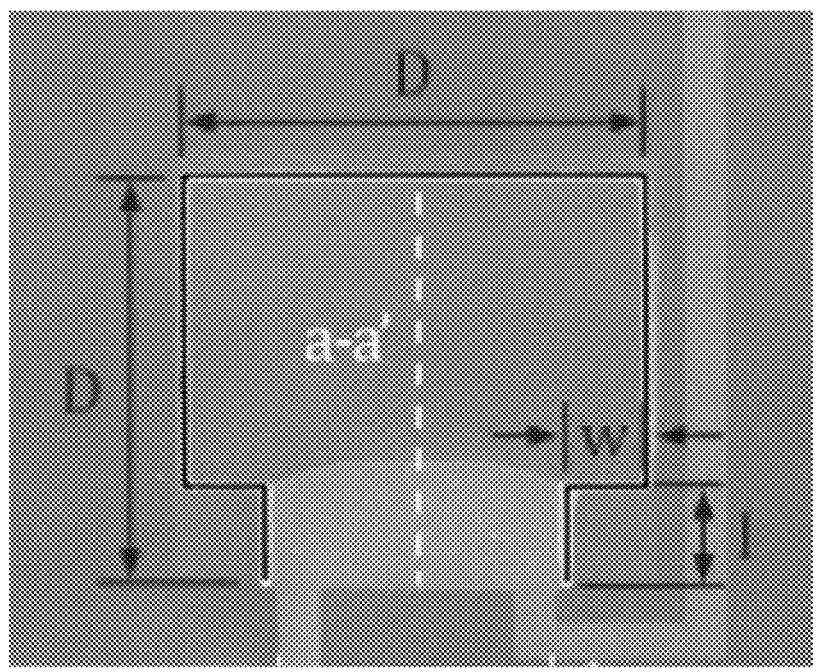
FIGS. 4A, 4B, and 4C: SEM images of fabricated paddle design with (A) geometric parameters and (B) primary features indicated. (C) Photograph of a completed 13-channel microphone array.
Figure 4B:
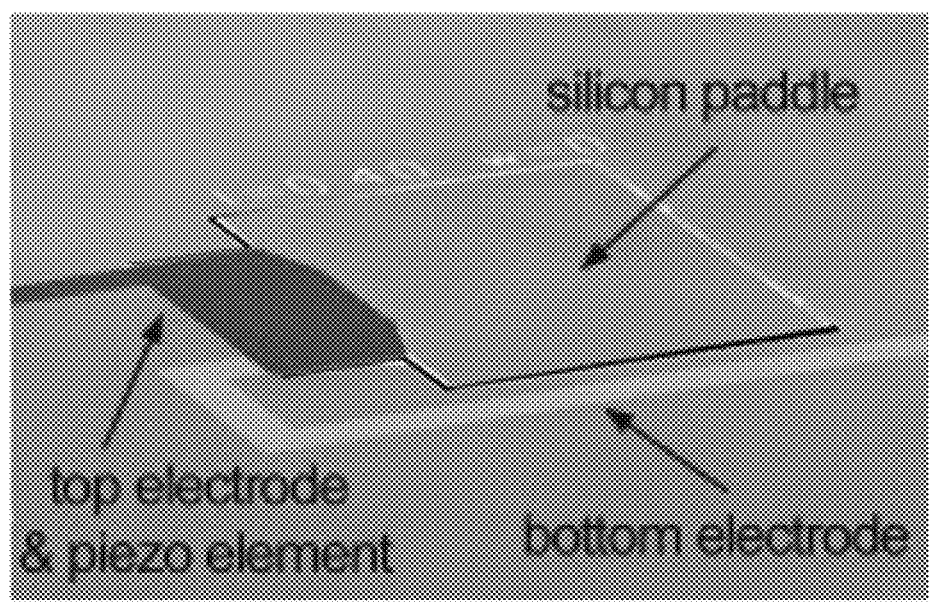
Figure 4C:
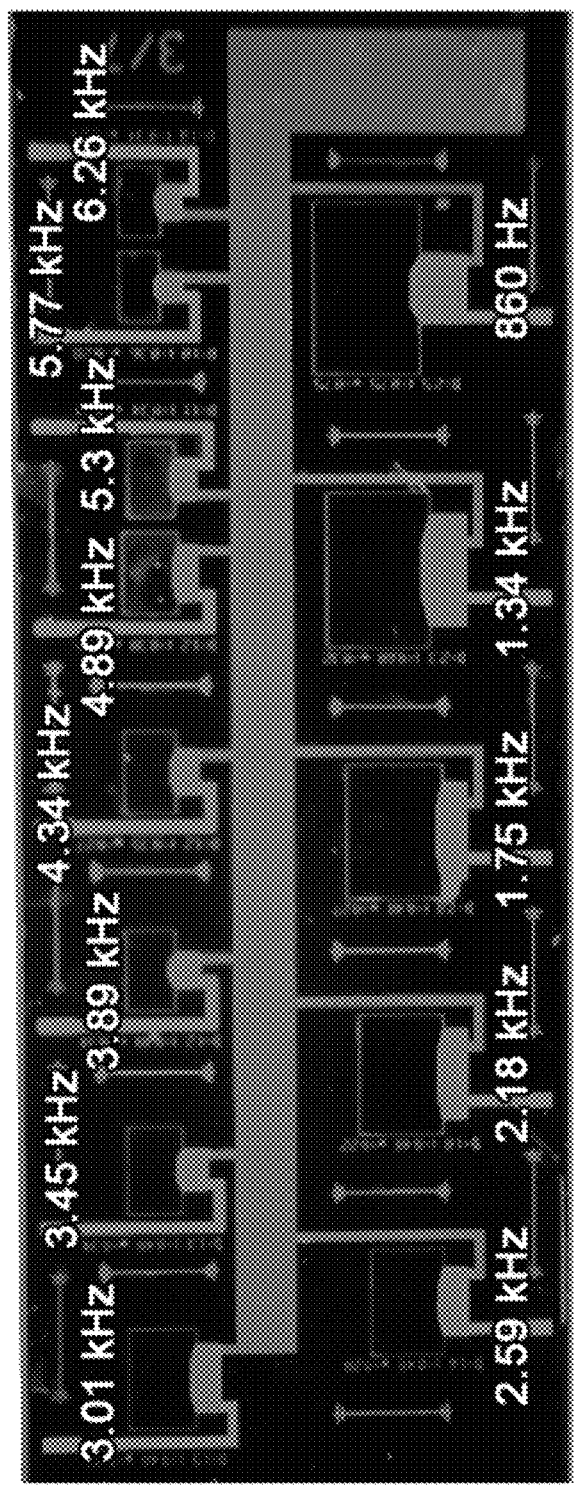

The sensing layers consist of evaporated top Al electrode 58 and bottom Al electrode 60, sputter-deposited zinc oxide 62 (ZnO, the active piezoelectric sensing material), and PECVD SiN 64 for electrical isolation. DRIE is used for the final release of the paddles 66 (FIG. 3D) to form a resonant microphone element 70 which is part of the array. A completed 13-channel array is shown in FIG. 4C.

Experimental Results

The experiments set forth below demonstrated the concept of automatic wheezing detection by integrating low power signal processing with the resonant microphone array using a Cypress Bluetooth LE Programmable-Radio-on-Chip (PRoC)

The respiratory monitoring system is based on an acoustic resonator array, composed of paddle-shaped piezoelectric cantilevers fabricated with a well-controlled fabrication method for accurate design of resonant frequencies and quality factors [1]. Though the number of the resonant microphones varies, the array that is presented here has 13 cantilevers with their resonant frequencies linearly-spaced between 860 and 6,260 Hz. The outlined fabrication process is CMOS compatible, so that processing electronics can be integrated on-chip in a commercial product.

Fabrication

The array is fabricated on a silicon-on-insulator (SOI) wafer 50 with 4.5 µm thick device layer (FIG. 3A). The SOI's oxide layer 52 is buried in silicon 54 serves as an etch-stop for anisotropic potassium hydroxide KOH backside etching as depicted in FIG. 3B. An SOI wafer is chosen as the substrate because of the accuracy and consistency of the SOI device layer thickness. This allows for reliable control of cantilever dimension and frequency characteristics.

The sensing layers consist of evaporated top Al electrode 58 and bottom Al electrode 60, sputter-deposited zinc oxide 62 (ZnO, the active piezoelectric sensing material), and PECVD SiN 64 for electrical isolation. DRIE is used for the final release of the paddles 66 (FIG. 3D) to form a resonant microphone element 70 which is part of the array. A completed 13-channel array is shown in FIG. 4C.

This microphone array uses a thin-film piezoelectric sensing mechanism, which can be implemented with very low power requirements and high sensitivity at the resonance frequency. With a cantilever design, we can make microphones with low resonant frequencies, which are needed to ensure signal filtering at those frequencies.

A pre-amplifier circuit is designed for a voltage gain of 0-40 dB on each channel using a simple non-inverting op-amp configuration. With a low-power op-Amp, such as the TLV342, each channel consumes about 0.24 mW. The diced microphone array is wire-bonded directly to the pre-amplifier PCB.

Figure 5:
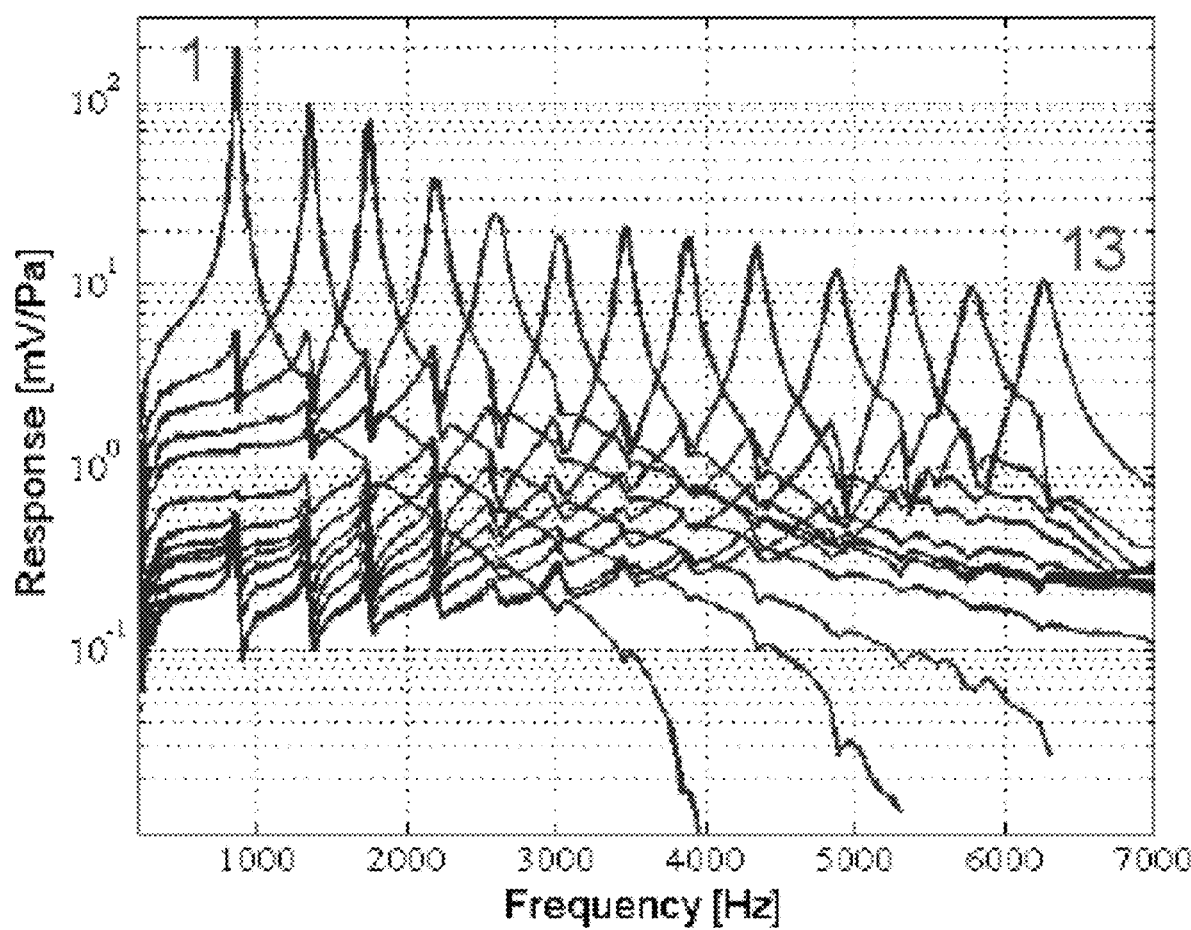
FIG. 5: Plot of measured sensitivities of the 13 channel microphone array (5 channels are implemented in the breathing classification study).

The selected geometric parameters and measured parameters are summarized in Table 1, and the measured frequency responses of the 13-channel array are plotted in FIG. 5.

TABLE 1

Summary of microphone array parameters and measurements for the five elements selected in the breathing classification study.

| | Microphone | | | | |
|---|---|---|---|---|---|
| | 2 | 4 | 7 | 9 | 12 |
| D (mm) | 2.3 | 1.8 | 1.3 | 1.2 | 1.0 |
| w (mm) | 0.32 | 0.22 | 0.34 | 0.27 | 0.28 |
| l (mm) | 0.6 | 0.4 | 0.4 | 0.35 | 0.36 |
| $f_0$ (Hz) | 1342 | 2179 | 3453 | 4341 | 5774 |
| Sensitivity (mV/Pa) | 102.4 | 39.4 | 21.1 | 17.0 | 9.78 |
| Q-Factor | 45.8 | 29 | 50.6 | 59.3 | 42.3 |

System Design

Many digital acoustic signal classification algorithms have been developed for high-degree-of-accuracy classification of acoustic features. Of these, most are poorly suited for embedded and wearable applications due to their large memory footprint or intensive computation requirements. Signature recognition algorithms are typically divided into two steps, feature extraction and classification, which are outlined for both a standard implementation and the developed resonant-array implementation below.

Feature Extraction

Cepstral features (used almost exclusively in commercial speech recognition algorithms) have been evaluated as very accurate (>95% accuracy) for breathing classification. Evaluation of cepstral features involve computationally intensive functions that can be avoided with the use of a pre-filtered array input.

Figure 6A:
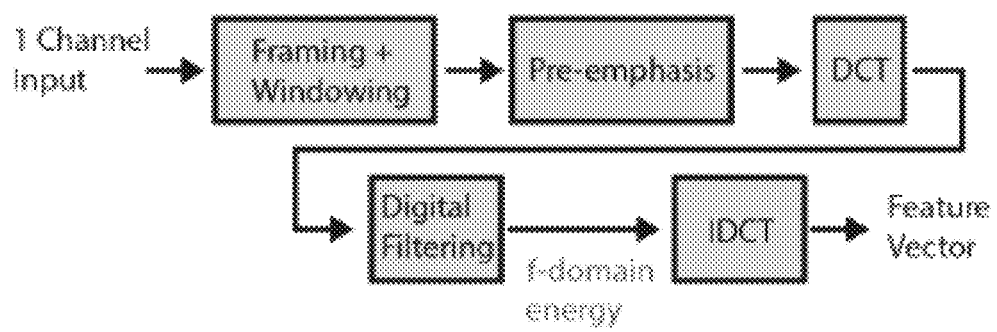
FIGS. 6A and 6B: Block diagrams of spectral feature extraction using (a) a single microphone input, and (b) a pre-filtered 5-element array input.

A block diagram of the traditional cepstral feature extraction is shown in FIG. 6A. The sensed signal is windowed. A filter is applied for pre-emphasis of high-frequency components. A discrete cosine transform (DCT) is applied to evaluate the real-spectrum of the signal, and digital filter banks are applied to estimate the energies at each filter bank frequency. The DCT can be evaluated in $O(n^2)$ instructions. The logarithm of the filter energies is passed through an inverse-DCT to transform them into the cepstral domain, and the first several cepstral features (4 for breathing classification) are taken as the resulting feature vector.

Figure 6B:
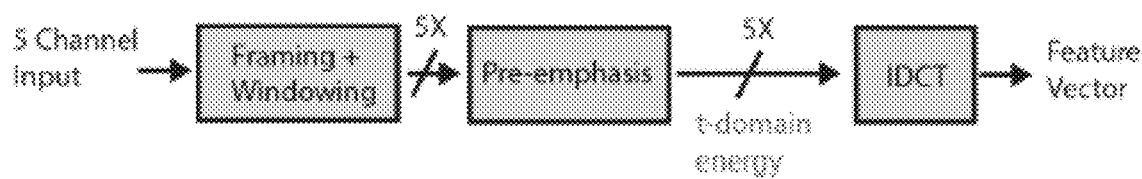

The modified feature-extraction approach with a 5-channel array input is illustrated in the block diagram in FIG. 6B. Use of the resonant microphone array for pre-filtering allowed us to remove the costly DCT and digital bandpass filtering steps, by direct calculation of filter energy from the time-domain signal, which reduces the computation to $O(n)$ instructions. This time-domain energy vector is identical in value to the frequency-domain energy vector, as shown by Parseval's theorem. This difference results in an estimated 95% reduction in computation time (and thus, about 15 times difference in power consumption) with a 10,240 S/sec sample rate.

Classifier Algorithm

A Naive Bayes classifier is selected as a simplified classification algorithm for the implementation of breathing recognition on a low-power microcontroller, due to memory (16 kB) and processing speed (32 MHz) constraints of the selected chip. A more complex classifier algorithm, which considers transient behavior, could be implemented to improve accuracy at the expense of battery life and processing speed. Several examples are Hidden-Markov Models (HMM), Artificial Neural Networks (ANN), and Support Vector Machines (SVM).

Experimental Results

Figure 7:
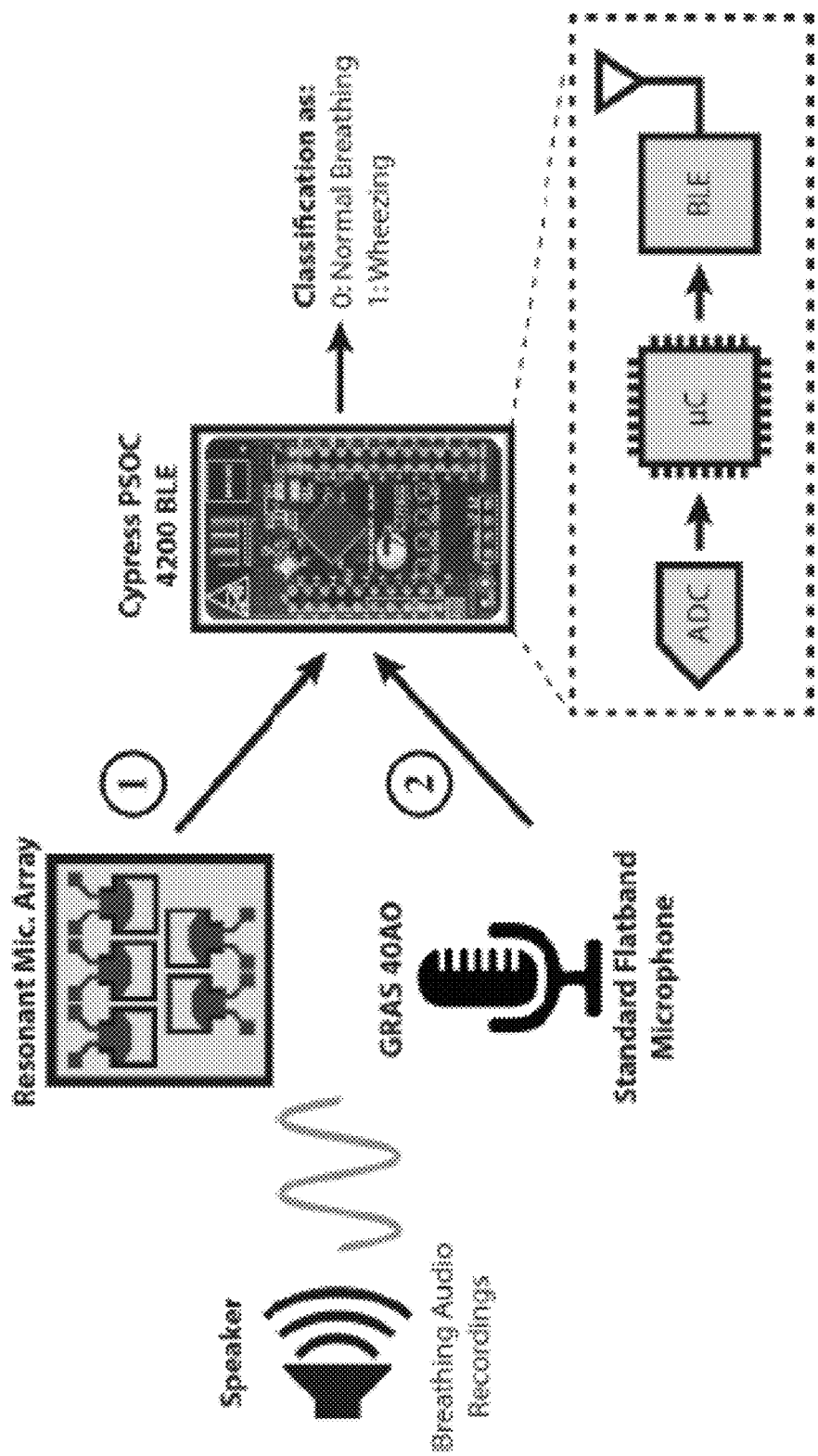
FIG. 7: Block diagram illustrating testing and on-chip processing steps for breathing classification.
Figure 8A:
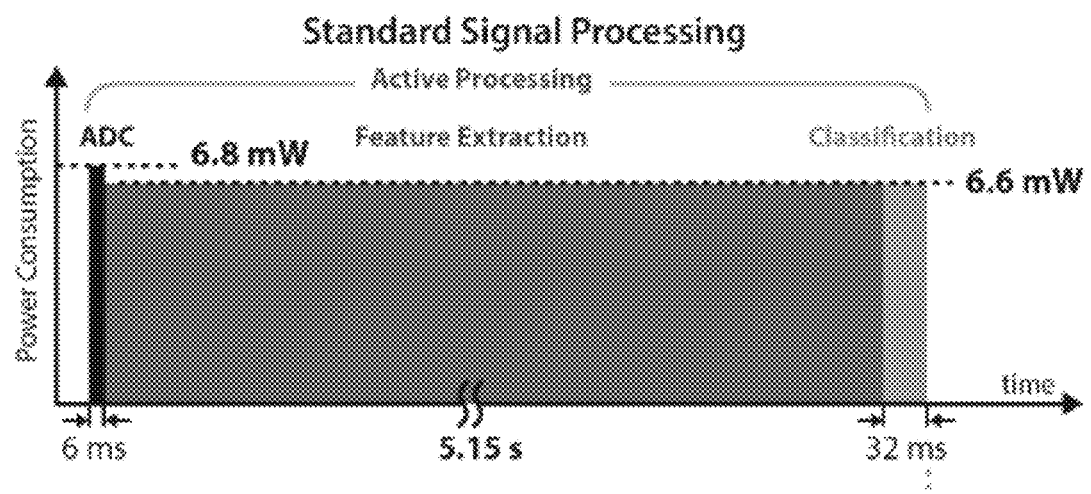
FIGS. 8A and 8B: Power consumption of Cypress PSoC 4200 and preamplifier electronics with (a) standard signal processing using a flat-band microphone, and (b) array signal processing demonstrating the reduced active processing cycle using pre-filtered microphone array.
Figure 8B:
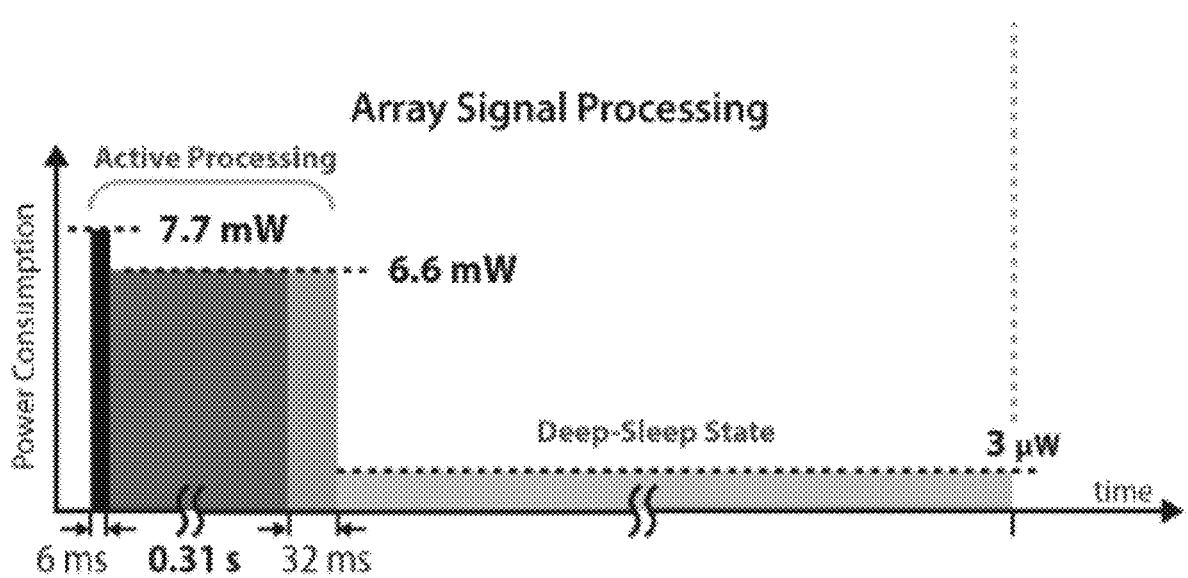

The concept of automatic wheezing detection is demonstrated by integrating low power signal processing with the resonant array using a Cypress Bluetooth LE Programmable-Radio-on-Chip (PRoC) with built-in ADC, ARM processor, radio, and antenna [2]. The BLE PRoC was configured for ultra-low power digitization of the sensor output, signal processing, and wireless output upon detection of a sensed signature of interest. The evaluation setup is shown in the system block diagram in FIG. 7.

The onboard 8 channel ADC (12 bit, 1 Msps) is used for digitization of the resonant microphones' signals. This corresponds to a 0.5 mV sampling resolution when using a 2V supply voltage.

Continuous pattern recognition is performed in the integrated ARM Cortex-M0 processor, which has a specified 0.9 DMIPS/MHz efficiency and a power requirement of 85 µW/MHz. Once a signal of interest is detected, the integrated Bluetooth Low Energy (BLE) transmitter and antenna sends a wireless notification, with an active power consumption of about 25 mW and a range of about 30 m. By duty cycling, this power consumption can be reduced to fit within the power constraints.

Each recognition cycle evaluated on the PSoC chip executes in an average of 5.19 seconds using a single input, and 0.35 seconds with an array input, equating to a 14.9 times difference in computation time. With duty cycling the active processing cycle and putting the device into a deep-sleep state for the remainder of the cycle, we demonstrate a 14.8 times difference in power consumption, with the newly invented approach consuming only 6.8% of the power taken by the standard approach (FIG. 6).

Figure 9:
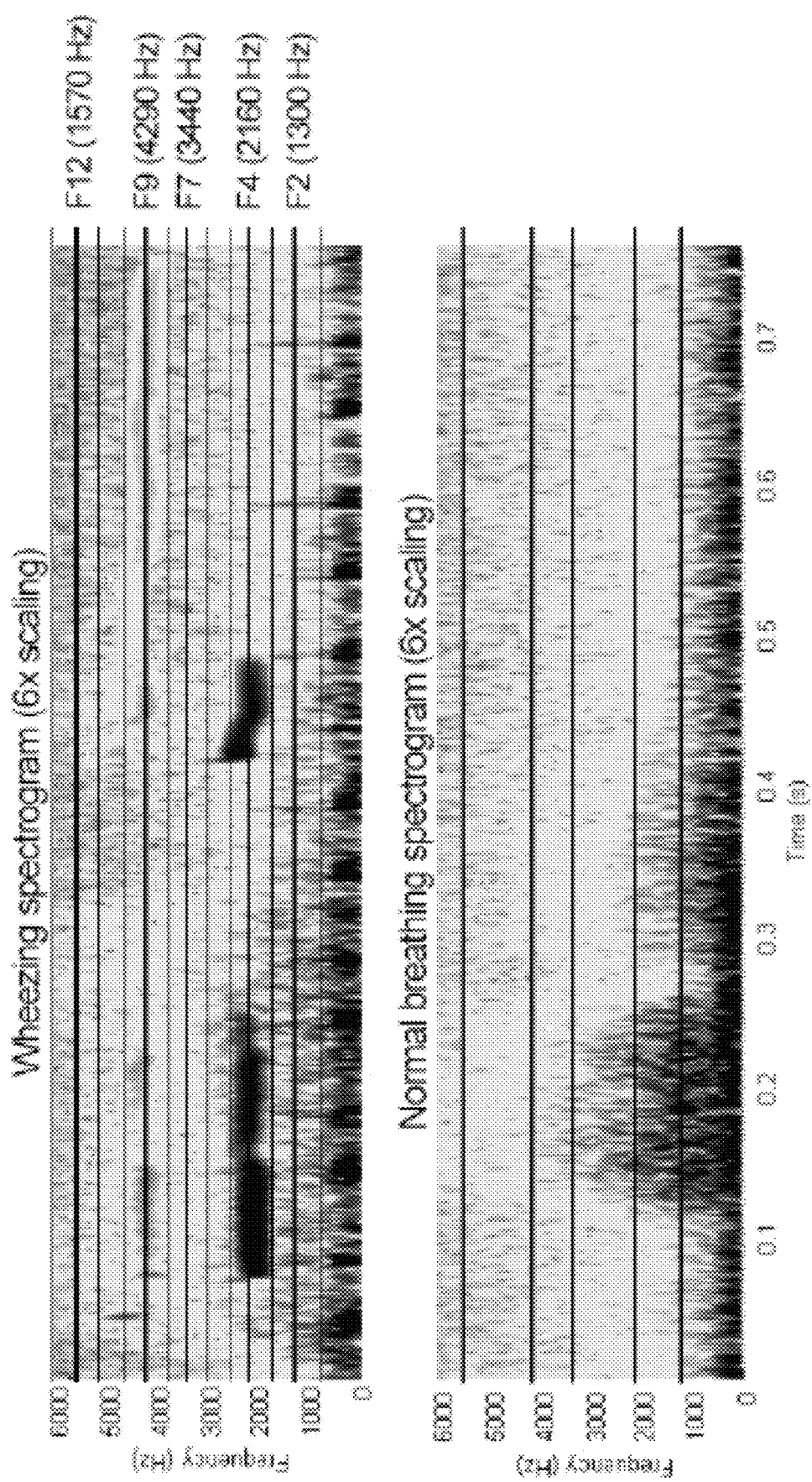
FIG. 9: Spectrograms showing relative spectral positions of breathing features and center frequencies of 5 selected MEMS microphone array elements. The red (i.e., darker) portions indicate high sound intensity and blue indicates low sound intensity.

Since acoustic emissions from the lungs generally occur in sub-kHz frequencies, and the fabricated microphone array spans the audible spectrum, a 6× scaling in frequency is applied to perform acquisition of breathing data with the array. The positions of the array resonant frequencies are shown relative to the scaled spectrograms for normal breathing and wheezing in FIG. 9.

Figure 10:
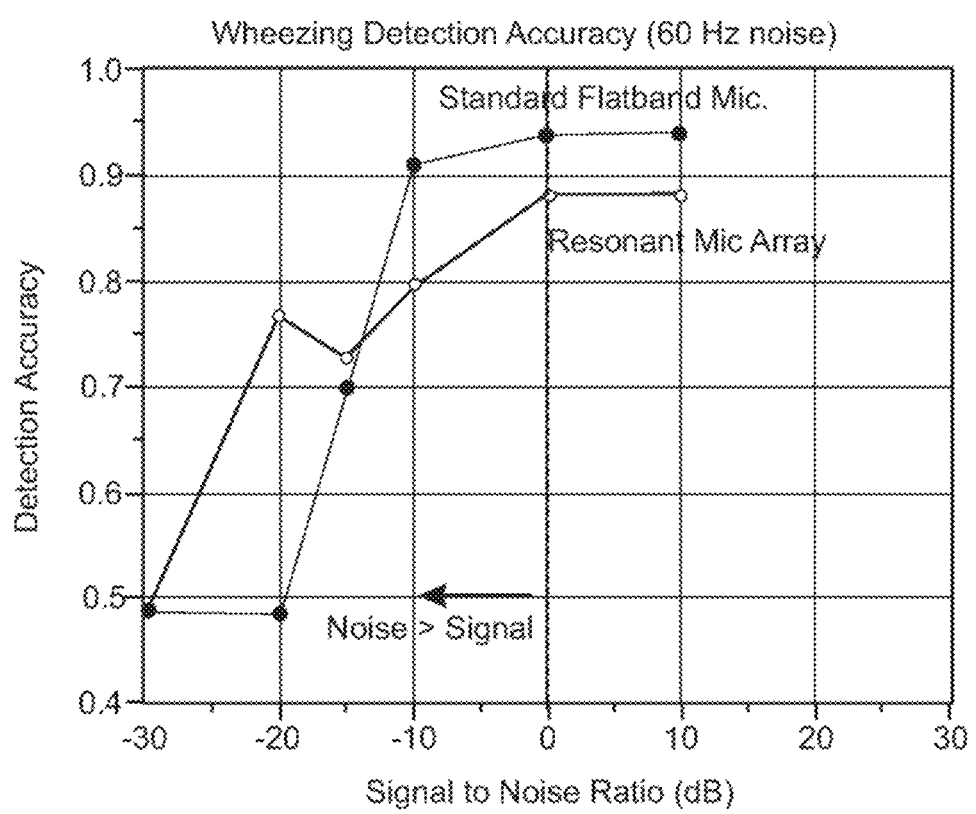
FIG. 10: Measured wheezing detection accuracies of the resonant microphone array and the reference microphone with various levels of 60 Hz sinusoidal background noise.
Figure 11:
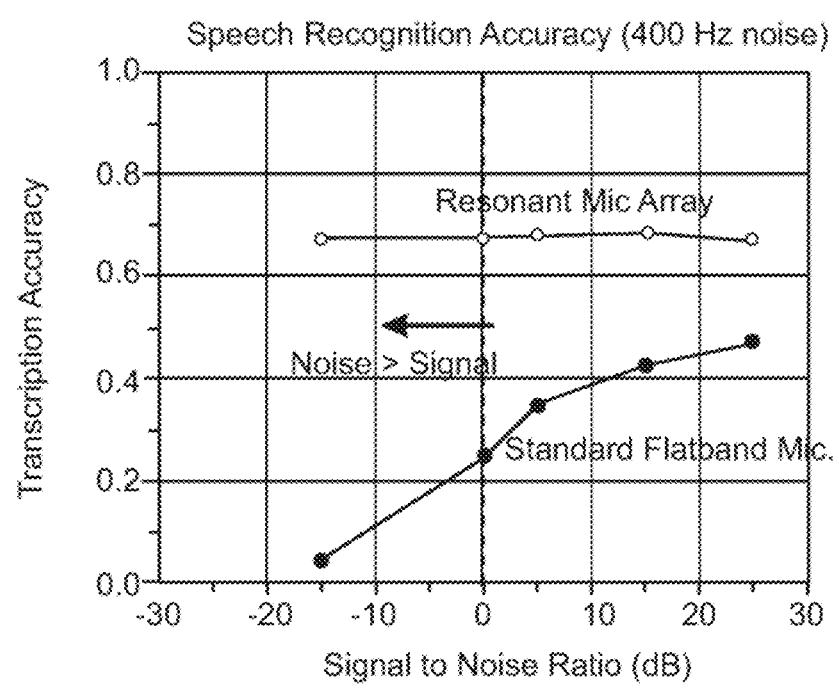
FIG. 11: Measured transcription accuracies of the resonant microphone array and the reference microphone used to process automatic speech recognition with various levels of 400 Hz sinusoidal noise.

The algorithm was evaluated using 6 wheezing and normal breathing audio recordings provided by the R.A.L.E. lung-sound repository (http://www.rale.ca/). The resulting classification accuracies are plotted in FIG. 10 for both the reference-microphone data and the resonant-microphone-array data under varying intensities of 60 Hz noise. The observed trend of noise-robust performance at large levels of out-of-band noise is consistent with that observed in automatic speech recognition experiments (FIG. 11), which showed a 63 percentage point increase in transcription accuracy (i.e., 68% vs 5%) for signal buried under noise with signal-to-noise ratio of −15 dB [3].

Summary

The embodiments set forth provide a respiratory monitoring system based on resonant microphone array acting as bank of acoustic bandpass filters. In particular, the use of an array of resonant microphones reduces the presence and influence of background noise in respiratory audio signal processing, and also reduces processing requirements and/or power consumption of lung sound signal processing is provided. Finally, a simplified feature extraction algorithm making use of pre-filtered acoustic signal is also provided.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

REFERENCES

[1] L. Baumgartel, A. Vafanejad, and E. S. Kim. "Resonance-enhanced piezoelectric microphone array for broadband or prefiltered acoustic sensing." Journal of microelectromechanical systems, 2012.
[2] A. A. Shkel, and E. S. Kim. "Wearable low-power wireless lung sound detection enhanced by resonant transducer array for pre-filtered signal acquisition." IEEE Transducers, 2017.
[3] A. A. Shkel, L. Baumgartel, and E. S. Kim. "A resonant piezoelectric microphone array for detection of acoustic signatures in noisy environments." IEEE Micro Electro Mechanical Systems (MEMS), 2015.

What is claimed is:

1. A method for continuous acoustic signature recognition and classification, comprising:
    obtaining an audio input signal from a resonant microphone array positioned proximate to a target, the audio input signal having a plurality of channels, the target producing characterizing audio signals depending on a state or condition of the target, wherein the resonant microphone array provides prefiltering of the audio input signals;
    extracting a plurality of acoustic features from the audio input signal with a signal processor, wherein the acoustic features are characterized by a unique distribution of acoustic energy in a time domain waveform, in a spectral domain, or in variation in the spectral domain over time, wherein extracting acoustic features from the audio input signal comprises directly calculating a plurality of filter energies at a plurality of filter bank frequencies from the time domain waveform without discrete cosine transform or digital bandpass filtering steps;
    classifying the plurality of acoustic features into acoustic classifications; and
    continuously monitoring the state of the target from the acoustic classifications.

2. The method of claim 1 wherein the target is a human subject and the audio input signal is produced by respiration, the resonant microphone array being positioned proximate to a human subject's chest to provide for monitoring respiration of the human subject.

3. The method of claim 1 wherein the resonant microphone array includes a plurality of resonant microphones.

4. The method of claim 1 wherein each resonant microphone has a resonant frequency such that resonant frequencies of a plurality of resonant microphones are spaced between 20 Hz and 12,000 Hz.

5. The method of claim 1 wherein the resonant microphone array includes a plurality of capacitive combinations of diaphragm and back plate for resonant microphones.

6. The method of claim 1 wherein the audio input signal is pre-filtered by the resonant microphone array to produce a pre-filtered audio input signal.

7. The method of claim 6 wherein the step of extracting a plurality of features from the audio input signal comprises:
    partitioning the pre-filtered audio input signal into one or more frames;
    applying a windowing function to each of the one or more frames of the pre-filtered audio input signal;
    performing pre-emphasis on the pre-filtered audio input signal that has been windowed and framed;
    transforming the pre-filtered audio input signal into a feature vector; and
    outputting the feature vector.

8. The method of claim 7 wherein transforming the pre-filtered audio input signal into the feature vector includes directly calculating a spectral energy of the pre-filtered audio input signal in the time domain.

9. The method of claim 7 wherein transforming the pre-filtered audio input signal into the feature vector includes applying an inverse discrete cosine transform and then calculating a vector of cepstral coefficients comprising the feature vector.

10. The method of claim 7 wherein a pre-emphasis network implements the step of performing pre-emphasis on the pre-filtered audio input signal.

11. The method of claim 7 wherein performing pre-emphasis on the pre-filtered audio input signal includes boosting one or more frequencies of the pre-filtered audio input signal relative to other frequencies of the pre-filtered audio input signal to minimize transmission distortion.

12. The method of claim 1 wherein classifying the plurality of acoustic features to determine the state of the target is performed by a classification algorithm.

13. The method of claim 12 wherein the classification algorithm is selected from the group consisting of Naive Bayes classifiers, Hidden-Markov Models, Artificial Neural Networks, and Support Vector Machines.

14. The method of claim 1 wherein the target is a fluid conduit.

15. The method of claim 1 wherein the step of monitoring the state of the target from the acoustic classifications includes a step of monitoring respiration in a mammalian subject.

16. The method of claim 15 wherein asthma and wheezing are monitored.

17. The method of claim 1 wherein the step of monitoring the state of the target from the acoustic classifications includes a step of automatically detecting medical acoustic signatures.

18. The method of claim 1 wherein the step of monitoring the state of the target from the acoustic classifications includes a step of monitoring heart sounds to detect murmurs.

19. An acoustic monitoring system, comprising:
a resonant microphone array configured to:
obtain an audio input signal having a plurality of channels, and
pre-filter the audio input signal through the resonant microphone array to form a pre-filtered audio input signal(s); and
a signal processor configured to:
divide the pre-filtered audio input signal into one or more frames,
windowing each of the one or more frames of the pre-filtered audio input signal,
transform the pre-filtered audio input signal into a feature vector that is outputted,
determine whether the audio input signal matches with a specific sound or sounds through a classification algorithm, wherein the feature vector includes acoustic features that are characterized by a unique distribution of acoustic energy in a time, domain waveform, in a spectral domain, or in variation in the spectral domain over time, wherein extracting acoustic features from the audio input signal comprises directly calculating a plurality of filter energies at a plurality of filter bank frequencies from the time domain waveform without discrete cosine transform or digital bandpass filtering steps, and
continuously monitor the state of a target by wirelessly sending the audio input signal or a notification of detection out to a nearby mobile phone or wireless transceiver.

20. The acoustic monitoring system of claim 19 wherein the classification algorithm is a machine-learning algorithm.

21. The acoustic monitoring system of claim 19 wherein the classification algorithm is selected from the group consisting of Naive Bayes classifiers, Hidden-Markov Models, Artificial Neural Networks, and Support Vector Machines.

22. The acoustic monitoring system of claim 19 wherein the resonant microphone array has a plurality of piezoelectric cantilevers or capacitive diaphragms or any other structures that form a plurality of resonant microphones that obtain audio signals and pre-filter the audio signals into a plurality of frequency bands.

23. The acoustic monitoring system of claim 22, wherein each resonant microphone or piezoelectric cantilever has a resonant frequency, wherein the resonant frequencies of the plurality of resonant microphones or piezoelectric cantilevers are spaced between 20 Hz and 12,000 Hz.

24. The acoustic monitoring system of claim 19 wherein the resonant microphone array includes a capacitive combination of diaphragm and back plate.

25. The acoustic monitoring system of claim 19 further comprising an adhesive layer or strap for attaching the resonant microphone array to a human subject.

\* \* \* \* \*